US006406631B1

(12) United States Patent
Collins et al.

(10) Patent No.: US 6,406,631 B1
(45) Date of Patent: *Jun. 18, 2002

(54) TWO STAGE DIAFILTRATION METHOD AND APPARATUS

(75) Inventors: Gregory R. Collins, Monroe; Edward C. Spence, Bronx, both of NY (US); James Summerton, Park Ridge, NJ (US)

(73) Assignee: Nephros, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/702,046

(22) Filed: Oct. 30, 2000

Related U.S. Application Data (63) Continuation-in-part of application No. PCT/US99/17468, filed on Jul. 30, 1999.

(51) Int. Cl.[7] .......................... B01D 61/24; B01D 61/28; B01D 61/32; B01D 63/00
(52) U.S. Cl. .................. 210/646; 210/143; 210/252; 210/321.6; 210/321.72; 210/323.2; 210/416.1; 210/645; 210/929
(58) Field of Search ................ 210/252, 416.1, 210/321.6, 321.72, 323.2, 645, 646, 929, 143; 604/4.01, 5.01

(56) References Cited

U.S. PATENT DOCUMENTS

| | | |
|---|---|---|
| 3,579,441 A | 5/1971 | Brown |
| 3,878,095 A | 4/1975 | Frasier et al. .................. 210/87 |
| 3,946,731 A | 3/1976 | Lichtenstein |
| 3,976,576 A | 8/1976 | Jacobsen et al. |
| 4,038,190 A | 7/1977 | Baudet et al. |
| 4,118,314 A | 10/1978 | Yoshida ........................ 210/22 |
| 4,134,834 A | 1/1979 | Brous ........................... 210/127 |

(List continued on next page.)

FOREIGN PATENT DOCUMENTS

| | | |
|---|---|---|
| EP | 0 018 734 | 11/1980 |
| EP | 0 076 422 | 4/1983 |
| EP | 0 516 152 | 12/1992 |
| EP | 0 890 368 | 1/1999 |
| EP | 0 960 624 | 12/1999 |
| WO | WO 92/11878 | 7/1992 |
| WO | WO 98/16171 | 4/1998 |

(List continued on next page.)

OTHER PUBLICATIONS

Ahrenholz R. et al., On–line hemodiafiltration with pre–and postdilution: a comparison of efficacy. The International Journal of Artificial Organs/vol. 20/No. 2, pp. 81–90 (1997).

Albertini, B. von, et al., High–Flux Hemodiafiltration: Under Six Hours/Week Treatment, vol. XXX Trans Am Soc Artif Intern Organs, 227–231 (1984).

Basile, Carlo et al., Plasma Volume Changes induced by Hypertonic Hemodiafiltration and Standard Hemodialysis, Am. J. Nephrol. 7: 264–269 (1987).

Basile, Carlo, et al., Hypertonic hemodiafiltration: A preliminary report on a cross–over study, Kidney International, vol. 33, Suppl. 24, pp. S–132–S–134 (1988).

(List continued on next page.)

*Primary Examiner*—John Kim
(74) *Attorney, Agent, or Firm*—Darby & Darby (57) ABSTRACT

In a blood dialysis system including a source of substitution fluid and a blood dialysis machine, a hemodiafiltration system comprises a first dialyzer including a first blood compartment having a first blood inlet which receives blood to be cleaned and a first blood outlet which expels partially diafiltered blood and a first dialysate compartment having a first dialysate inlet and a first dialysate outlet, means for mixing the partially diafiltered blood with substitution fluid from the source to obtain a blood/substitution fluid mixture, and a second dialyzer including a second blood compartment having a second blood inlet which receives the blood/substitution fluid mixture and a second blood outlet which expels diafiltered blood and a second dialysate compartment having a second dialysate inlet and a second dialysate outlet.

33 Claims, 9 Drawing Sheets

U.S. PATENT DOCUMENTS

| | | | |
|---|---|---|---|
| 4,219,422 A | 8/1980 | Knothe et al. | 210/137 |
| 4,381,999 A | 5/1983 | Boucher et al. | 210/637 |
| 4,498,990 A | 2/1985 | Shaldon et al. | 210/637 |
| 4,647,378 A | 3/1987 | Minami | 210/646 |
| 4,702,829 A | 10/1987 | Polaschegg et al. | 210/195.2 |
| 4,708,802 A | 11/1987 | Rath et al. | 210/641 |
| 4,722,798 A | 2/1988 | Goss | 210/646 |
| 4,770,769 A | 9/1988 | Schael | 210/96.2 |
| 4,834,888 A | 5/1989 | Polaschegg | 210/646 |
| 4,861,485 A | 8/1989 | Fecondini | 210/641 |
| 5,011,607 A | 4/1991 | Shinzato | 210/637 |
| 5,069,788 A | 12/1991 | Radovich et al. | 210/321.8 |
| 5,075,003 A | 12/1991 | Aoyagi | 210/321.8 |
| 5,178,763 A | 1/1993 | Delaunay | 210/644 |
| 5,194,157 A | 3/1993 | Ghezzi et al. | 210/646 |
| 5,211,849 A | 5/1993 | Kitaevich et al. | 210/645 |
| 5,244,568 A | 9/1993 | Lindsay et al. | 210/87 |
| 5,318,750 A | 6/1994 | Lascombes | 422/81 |
| 5,431,811 A | 7/1995 | Tusini et al. | 210/90 |
| 5,476,592 A | 12/1995 | Simard | 210/651 |
| 5,487,827 A | 1/1996 | Peterson et al. | 210/87 |
| 5,511,875 A | 4/1996 | Jonsson et al. | 366/136 |
| 5,578,223 A | 11/1996 | Bene et al. | 210/85 |
| 5,660,722 A | 8/1997 | Nederlof | 210/90 |
| 5,690,831 A | 11/1997 | Kenley et al. | 210/646 |
| 5,702,597 A | 12/1997 | Chevallet et al. | 210/195.2 |
| 5,711,883 A | 1/1998 | Folden et al. | 210/646 |
| 5,725,775 A | 3/1998 | Bene et al. | 210/646 |
| 5,808,181 A | 9/1998 | Wamsiedler et al. | 73/38 |
| 5,846,419 A | 12/1998 | Nederlof | 210/323.1 |
| 5,871,694 A | 2/1999 | Beden et al. | 422/44 |
| 6,039,877 A | 3/2000 | Chevallet et al. | 210/636 |
| 6,139,748 A | 10/2000 | Ericson et al. | 210/646 |
| 6,200,485 B1 | 3/2001 | Kitaevich et al. | 210/739 |

FOREIGN PATENT DOCUMENTS

| | | |
|---|---|---|
| WO | WO 98/16269 | 4/1998 |
| WO | WO 98/35710 | 8/1998 |
| WO | WO 98/50090 | 11/1998 |
| WO | WO 00/44478 | 8/2000 |

OTHER PUBLICATIONS

Canaud, B., et al., Hemodiafiltratyion with On–Line Production of substitution Fluid: Long–Term Safety and Quantitative Assessment of Efficacy, Maeda K. Shinzato T (eds): Effective Hemodiafiltration: New Methods. Conrib Nephrol. Basel, Karger, vol. 108. pp 12–22 (1994).

Ghezzi, P.M. et al., Hemodiafiltration Without Replacement Fluid, ASAIO Journal, 61–65 (1992).

Ghezzi, P.M. et al., Use of the ultrafiltrate obtained in two–chamber (PFD) hemodiafiltration as replacement fluid. Experimental ex vivo and in vitro study. The International Journal of Artificial Organs/vol. 14/No. 6, 1991/pp. 327–334.

Limido, D. et al., Clinical evaluation of AK 100 ULTRA for predilution HF with on–line prepared bicarbonate substitution fluid. Comparison with HD and acetate postdilution HF. The International Journal of Artificial Organs/vol. 20/No. 3, 1997/pp. 153–157.

Maeda, Kenji, et al., Push/Pull Hemodiafiltration: Technical Aspects and Clinical Effectiveness, Nephron 71:1–9 (1995).

Man, N. K., et al., Acetate–Free Biofiltration: State of the Art, Hemodiafiltration: New Methods. Contrib Nephrol. Basel, Karger, vol. 108, pp. 87–93 (1994).

Marangoni Roberto, et al., Short Time Treatment with high–Efficiency Paired Filtration Dialysis for Chronic Renal Failure, Artificial Organs, 547–552, Blackwell Scientific Publications, Inc., Boston International Society for Artificial Organs (1992).

Miller, J. H., et al., Technical Aspects of High–Flux Hemodiafiltration of Adequate short (Under 2 Hours) Treatment, the Department of Medicine, Wadsworth V.A. medical Center, and UCLA school of; medicine, Los Angeles, California, pp. 377–380 (1984).

Ono Masataka, et al. Comparison of Types of On–line Hemodiafiltration from the Standpoint of Low–Molecular–Weight Protein Removal, Contrib Nephrol. Basel, Karger, vol. 108. pp 38–35 (1994).

Polaschegg Hans–Dietrich, et al., Hemodialysis Machines and Monitors, pp 333–379 (undated).

Ronco, C. et al., Comparision of four different short dialysis techniques. The International Journal Of Artificial Organs/vol. 11/No. 3, pp 169–174, (1988).

Ronco, C. et al., Paired Filtration dialysis: Studies on Efficiency, Flow Dynamics and Hydraulic Properties of the System, Blood Purif 8:126–140, (1990).

Ronco, C. et al., Technical and Clinical Evaluation of Different short, Highly Efficient Dialysis Techniques, Contr. Nephrol., vol. 61, pp. 46–68 (Karger, Basel 1988).

Rotellar Emilio, Large–Surface Hemodialysis, Artificial Organs, 387–396, Raven Press, New York, International society for Artificial Organs, (1986).

Sanz–Moreno C. et al., Hemodiafiltration in Two Chambers Without Replacement Fluid: A Clinical Study. Artificial Organs, 19(5): 407–410, Blackwell Science, Inc., Boston International Society for Artificial Organs (1995).

Shaldon S., Mixed Hemofiltration (MHF): 18 Months Experience With Ultrashort Treatment Time, vol. XXV11 Trans Am Soc Artif Intern Organs, pp. 610–612, (1981).

Shinaberger James H. et al., Short Treatment 16: pp. 360–381.

Shinzato, et al., Newly Developed Economical and Efficient Push/Pull Hemodiafiltration, Maeda K. Shinzato T(eds): Effective Hemodiafiltration: New Methods. Contrib Nephrol Basel, Karger, vol. 108, pp. 79–86 (1994).

Sternby Jan, A Decade of Experience with On–Line Hemofiltration/Hemodiafiltration, Maeda K. Shinzato T (eds): Effective Hemodiafiltration: New Methods. Contrib Nephrol Basel, Karger, vol. 108, pp. 1–11 (1994).

TWO STAGE DIAFILTRATION METHOD AND APPARATUS

RELATED APPLICATIONS

This application is a continuation-in-part of International Application PCT/US99/17468, filed Jul. 30, 1999, the entire disclosure of which is incorporated herein by reference.

FIELD OF THE INVENTION

The invention relates to blood cleansing systems in general and, more particularly, to a blood cleansing modality commonly referred to as hemodiafiltration.

BACKGROUND OF THE INVENTION

Hemodiafiltration combines both standard dialysis and hemofiltration into one process, whereby a dialyzer cartridge containing a high flux membrane is used to remove substances from the blood both by diffusion and by convection. The removal of substances by diffusion is accomplished by establishing a concentration gradient across a semipermeable membrane by flowing a dialysate solution on one side of the membrane while simultaneously flowing blood on the opposite side of the membrane. In existing systems, to enhance removal of substances using hemodiafiltration, a solution called substitution fluid is continuously added to the blood either prior to the dialyzer cartridge (pre-dilution) or after the dialyzer cartridge (post-dilution). An amount of fluid equal to that of the added substitution fluid is ultrafiltered across the dialyzer cartridge membrane carrying with it additional solutes.

Substitution fluid is usually purchased as a sterile/non-pyrogenic fluid contained in large flexible bags or is produced on-line by filtration of a non-sterile dialysate through a suitable filter cartridge rendering it sterile and non-pyrogenic Techniques for online production of substitution fluid have been described in the literature, for example, in D. Limido et al., "*Clinical Evaluation of AK-100 ULTRA for Predilution HF with On-Line Prepared Bicarbonate Substitution Fluid. Comparison with HD and Acetate Postdilution HF*", *International Journal of Artificial Organs,* Vol. 20, No. 3 (1997), pp. 153–157.

In general, existing hemodiafiltration schemes use a single dialyzer cartridge containing a high flux semi-permeable membrane, for example see P. Ahrenholz et al., "*On-Line Hemodiafiltration with Pre- and Postdilution: A Comparison of Efficiency*", *International Journal of Artificial Organs,* Vol. 20, No. 2 (1997), pp. 81–90. In prior art systems, substitution fluid is introduced into the blood stream either in a pre-dilution mode or in a post-dilution mode relative to the dialyzer cartridge. The preferred mode for maximal removal of both small and large substances from blood, in accordance with the prior art, is the post-dilutional mode because this mode achieves the highest concentration gradient between the blood and the dialysate fluid. In a typical pre-dilution mode with on-line generation of substitution fluid, however, the bloodside concentration is lowered relative to the dialysate fluid. As a result, removal (or clearance) of substances can decrease, as described in The International Journal of Artificial Organs, vol. 20, pp. 81–90. This decrease is particularly apparent for smaller molecules, like urea, where mass transport is driven more by diffusion than by convection. Use of two dialyzer cartridges in a hemodiafiltration scheme has been reported in J. H. Miller et al., "*Technical Aspects of High-Flux Hemodiafiltration for Adequate Short (Under 2 Hours) Treatment*", *Transactions of the American Society Artificial Internal Organs* (1984), pp. 377–380. In this scheme, the substitution fluid is reverse-filtered through the membrane of the first dialyzer cartridge. A variation of this method is described in B. Nederlof, "HEMO(DIA)FILTRATION APPARATUS AND FILTRATE FLOW REGULATOR", U.S. Pat. No. 5,660,722 (1997), where a dialysate pump between the dialyzers is used to regulate the amount of reverse-filtration in the second dialyzer cartridge.

Certain trade-offs exist with respect to removal of different size molecules when comparing pre-dilution diafiltration and post-dilution diafiltration using a single dialyzer cartridge. For example, on-line pre-dilution diafiltration schemes generally achieve higher convection filtration rates, compared to on-line post-dilution diafiltration, enhancing removal of large molecules; however, the increased removal by convection comes at the expense of reducing the removal of small molecules, such as urea and creatinine. In on-line post-dilution diafiltration schemes, on the other hand, the amount of fluid that may be filtered from the blood as it passes through the dialyzer cartridge is limited. Specifically, the filterable amount is dependent upon several factors, which include blood flow rate, blood hematocrit, and blood protein concentration. Typically, the filterable amount is 20% to 30% of the incoming blood flow rate. For example, at a blood flow rate of 300 milliliter per minute (ml/min), the filterable amount is typically limited to 90 ml/min. In the two dialyzer approach, the filterable amount is also limited to about 20% to 30% of the blood flow because forward filtration occurs only in the first dialyzer. The second dialyzer then re-infuses the fluid lost in the first dialyzer by reverse-filtration, as in on-line post-dilution diafiltration.

SUMMARY OF THE INVENTION

This invention seeks to provide a hemodiafiltration method and apparatus that overcomes the convection limitation associated with on-line post-dilution diafiltration schemes using a single dialyzer cartridge, as well as the loss of small molecule clearance associated with on-line pre-dilution diafiltration schemes using a single dialyzer cartridge.

It is an object of the present invention to provide an improved method of hemodiafiltration using two dialyzer cartridges or a single cartridge having two dialyzer stages. In addition, the present invention provides methods and systems for regulating the amount of ultrafiltration in each of the two dialyzers. It will be understood by persons of ordinary skill in the art that, although the invention is described herein in the context of hemodiafiltration using substitution fluid which is produced "on-line", the hemodiafiltration methods and systems of the invention can be readily modified to be used in conjunction with other sources of substitution fluid.

According to an aspect of the invention, a hemodiafiltration system includes at least two dialyzer cartridges, or a single cartridge with at least two dialyzer stages, which perform diafiltration, and at least one sterility filter which converts dialysate fluid into a sterile substitution fluid, preferably on-line. Additional components (e.g. pumps, check valves, mixing chambers, control units) may also be used in conjunction with the invention, as described below.

Each dialyzer contains a semi-permeable membrane that is embedded within a jacket or housing. The semi-permeable membrane separates the device into a blood compartment and a dialysate compartment. At least two dialyzer cartridges are used to carry out the diafiltration process in accordance with the invention. Alternatively, the two dialyzer cartridges may be combined into a single cartridge including two dialyzer sections. The at least one sterility filter cartridge preferably also contains a semi-permeable membrane. This filter is used to remove bacteria, endotoxins, and other particulate from dialysate in order to generate a suitable substitution fluid stream, preferably on-line.

During operation of the system, blood enters the bloodside compartment of the first dialyzer cartridge, wherein a portion of plasma water is filtered across the semi-permeable membrane into the adjacent dialysate compartment. Upon exiting the first dialyzer cartridge, substitution fluid is added back to the blood at a rate higher than the rate at which fluid is filtered out of the blood in the first dialyzer cartridge. The diluted blood then enters the bloodside compartment of the second dialyzer cartridge, wherein additional plasma water is filtered across the semi-permeable membrane into the adjacent dialysate compartment at a rate substantially equal to the difference between the rate at which substitution fluid is added to the blood upon exiting the first dialyzer cartridge and the filtration rate at the first dialyzer. Thus, the substitution fluid acts as a post-dilution fluid relative to the first dialyzer cartridge as well as a pre-dilution fluid relative to the second dialyzer cartridge. The advantage of operating the system in this mode is that the loss of small molecular weight clearance due to the diluted fluid entering the second dialyzer cartridge is compensated by a gain in small molecular weight clearance in the first dialyzer cartridge. Clearance of larger molecular weight substances is further enhanced because the total filtration of plasma water can be effectively increased (e.g., 40% to 100% of the incoming blood flow rate) compared to that of a single dialyzer cartridge operating in a post-dilution mode or two dialyzers in series with the second dialyzer being operated in a reverse-filtration mode.

Dialysate fluid for the system of the invention may be generated using existing methods. The dialysate fluid enters the second dialyzer cartridge and flows counter-current with respect to the blood flow direction. The dialysate fluid acts to set-up a concentration gradient against the bloodside fluid, thereby inducing diffusion of solutes across the semi-permeable membrane. As the dialysate traverses through the dialysate compartment, the dialysate flow rate increases due to plasma water being filtered across into the dialysate compartment as described above. Upon exiting the second dialyzer, the dialysate fluid enters the first dialyzer cartridge, flowing counter-current with respect to the bloodside fluid. The dialysate flow rate increases as the dialysate flows through the dialysate compartment, due to filtration of plasma water across the semi-permeable membrane. Upon exiting the dialyzer cartridge, the spent or used dialysate is transported back to the dialysis machine. By including additional components, for example, an inter-stage pump located either in the dialysate path between the two dialyzers or in the blood path between the two dialyzers, it is possible to regulate the amount of plasma water filtered across the membranes of the respective cartridges. This improved control enables the system to achieve even higher effective substitution rates.

Preparation of the sterile/non-pyrogenic substitution fluid may be accomplished by drawing a portion of fresh dialysate solution from a fresh dialysate inlet line and passing it through at least one sterile filter cartridge prior to introducing it into the blood between the two dialyzer stages. In the present invention, the dialysis machine generally performs all of its normal functions, such as preparing dialysate, metering dialysate flow rate, balancing flow, monitoring pressures, ultrafiltration control, monitoring spent dialysate for presence of blood etc.

The present invention may be implemented in a number of ways. In one embodiment, substitution fluid is added to the blood between the two dialyzer stages without additional components to regulate the filtration in each stage. In a second and third embodiment, an inter-stage dialysate pump is added as a means for controlling the relative filtration rates of the two dialyzer stages. In the second embodiment, a feedback control loop based on pressure inputs is used as means for balancing the transmembrane pressure (TMP) of each dialyzer. In the third embodiment, a feedback control loop based on a measured inter-stage flow rate is used. In a fourth embodiment, a positive displacement pump is used as an inter-stage dialysate pump, and a feed forward control loop is used to regulate the relative filtration rates of the two dialyzers. In a fifth embodiment, a check valve is used to shunt the flow past the inter-stage dialysate pump. The advantage of this last embodiment is that the check valve simplifies the control loop for operating the inter-stage dialysate pump. A sixth and seventh embodiment of the invention are generally similar to the fourth and fifth embodiments, respectively, except for the fact that an inter-stage blood pump is used instead of an inter-stage dialysate pump. Finally, in an eighth embodiment of the invention, the inter-stage pump is controlled by a feedback loop based on measurement of inter-stage blood hematocrit.

DETAILED DESCRIPTION OF THE INVENTION

Figure 1:
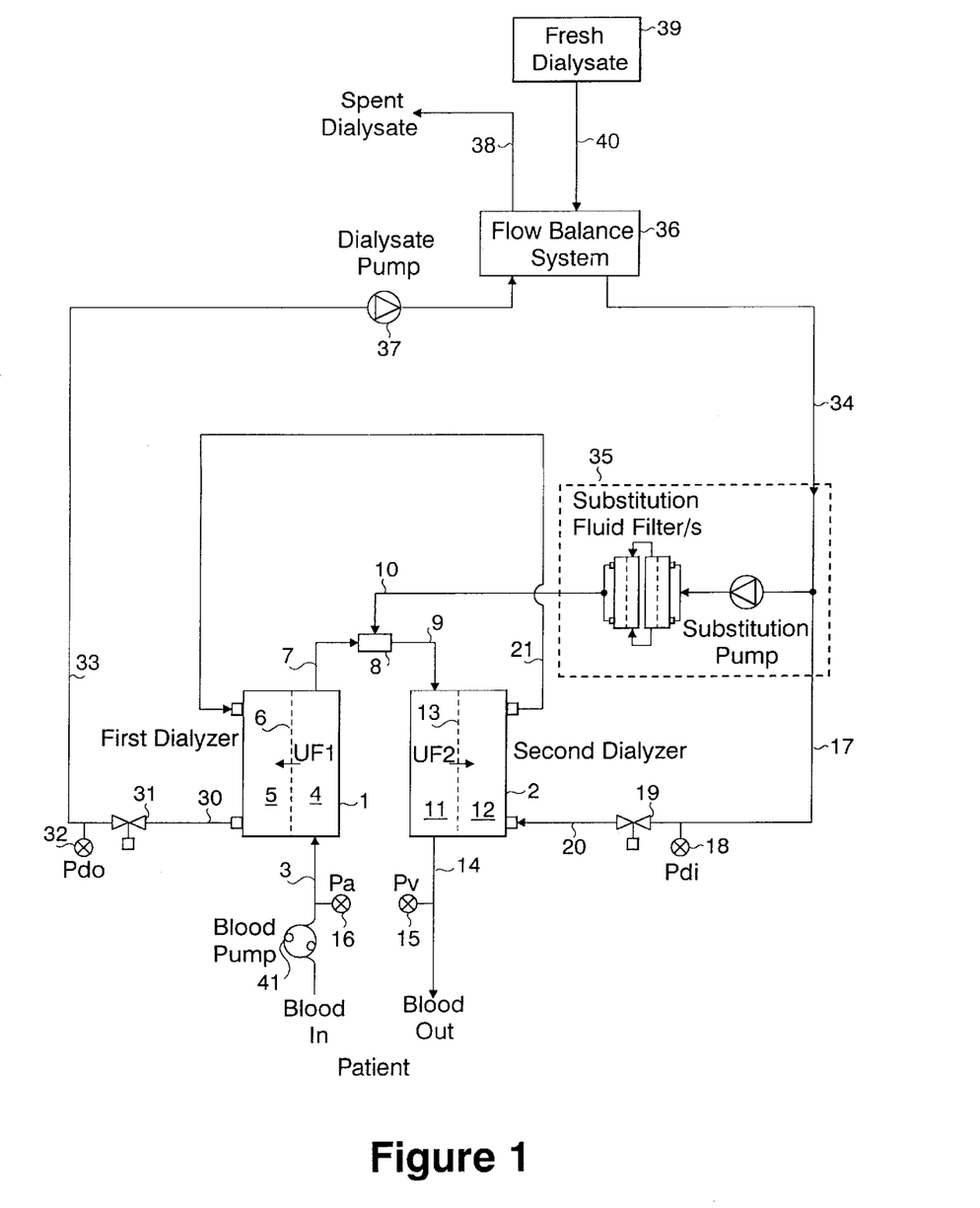
FIG. 1 is a schematic illustration of a two stage hemodiafiltration system in accordance with an embodiment of the invention.

In the embodiment of FIG. 1, blood to be cleaned 3 is pumped by a blood pump 41 and enters a first dialyzer cartridge 1. As shown in FIG. 1, inlet blood circuit pressure 16 (denoted "Pa") is measured upon exiting blood pump 41, to be used as a monitoring and control parameter of the blood flow prior to entering the first dialyzer cartridge. The blood carrying tubing may be any bloodline tubing known in the art, for example a flexible polyvinylchloride (PVC) tubing. The blood flow rate is generally in the range of about 200 to about 700 ml/min, preferably 300 to 600 ml/min.

Dialyzer cartridge 1 contains a semi-permeable membrane 6 that divides the dialyzer into a blood compartment 4 and a dialysate compartment 5. As blood passes through the blood compartment, plasma water containing blood substances in filtered across the semi-permeable membrane (denote "UF1" in FIG. 1). Additional blood substances are transferred across the semi-permeable membrane by diffusion which is induced by a difference in concentration between the blood compartment and the dialysate compartment. The dialyzer cartridge used may be of any type suitable for hemodialysis, hemodiafiltration, hemofiltration, or hemoconcentration, as are known in the art. Preferably, the dialyzer contains a medium or high flux membrane. Examples of suitable cartridges include but are not limited to the Fresenius F60, Baxter CT 110, Hospal Filtral 16, or Minntech Hemocor HPH 1000.

Partially diafiltered blood 7 exits dialyzer cartridge 1 and mixes with sterile substitution fluid 10 in a mixing chamber 8. The blood/substitution fluid mixture 9 then enters a second dialyzer cartridge 2. The second dialyzer cartridge contains a semi-permeable membrane 13 that divides the dialyzer into a blood compartment 11 and a dialysate compartment 12. As blood passes through blood compartment 11, plasma water containing blood substances is filtered across the semi-permeable membrane (noted as UF2). Additional blood substances are transferred across the semi-permeable membrane by diffusion due to concentration gradients between the blood and dialysate compartments. The second dialyzer cartridge can be of any type used for hemodialysis, hemodiafiltration, hemofiltration, or hemoconcentration. Preferably the dialyzer contains a medium or high flux membrane. Examples of the suitable cartridges include but are not limited to the Fresenius F60, Baxter, Conn. 110, Hospal Filtral 16, or Minntech Hemocor HPH 400. The cleansed blood 14 is returned to the patient (not shown) through bloodline PVC tubing, as is known in the art. Pressure of the exiting blood may also be monitored through a pressure sensor 15.

Fresh dialysate solution 39 may be prepared using any method known in the art, for example the volumetric proportioning method used in the Fresenius 2008 dialysis machine, available from Fresenius, Lexington, Mass., USA. Dialysate fluid is conveyed to a flow balancing system 36 via fluid path 40. The flow balancing system 36 may include any suitable devices known in the art, for example, volumetric balance chambers as used in the Fresenius 2008 dialysis machine, or dual flow meters as used in the Baxter 1550 dialysis machine, available from Baxter, Deerfield, Ill., USA. Fresh dialysate from the flow balance system flows through a conduit 34. A portion of the fresh dialysate fluid may be used as raw substitution fluid for an on-line substitution fluid delivery system 35, which may include any suitable substitution fluid delivery system known in the art. The remaining dialysate fluid 17, not used for producing substitution fluid, enters the dialysate inlet port of the second dialyzer cartridge 2. The pressure of the inlet dialysate fluid may be measured by a pressure sensor 18 (the pressure denoted "Pdi"). The fresh dialysate fluid 20 enters the dialysate compartment 12 and flows counter current with respect to the blood flow in the adjacent compartment. During diafiltration, plasma water filters across the semi-permeable membrane 13 and mixes with the dialysate fluid. A mixture of the dialysate fluid and the filtered plasma water exits the second dialyzer cartridge 2 and flows through a conduit 21 that leads to the inlet dialysate port of first dialyzer cartridge 1. The dialysate fluid entering dialysate compartment 5 of first dialyzer cartridge 1 flows countercurrent with respect to the blood flow in the adjacent compartment. Plasma water filtered across the semi-permeable membrane 6 is mixed with the dialysate fluid. The used or spent dialysate fluid exits first dialyzer cartridge 1 and flows through a conduit 30 that leads back to flow balance system 36. Pressure of the spent dialysate fluid may be measured by a pressure sensor 32 (measuring pressure "Pdo").

It will be apparent to those skilled in the art that the hemodiafiltration method and system of the present invention is significantly more efficient than current methods and systems using a single dialyzer, in both pre- and post-dilution modes of operation, as well as methods using two dialyzers, performing forward filtration and reverse-filtration, respectively. An advantage of the system of the present invention is the ability to achieve higher substitution rates than the rates achieved by prior art systems and methods. The present invention overcomes the limitation of the prior art systems, in which not more than about 30% of the incoming blood flow may be filtered by a single cartridge before adding substitution fluid. In prior art systems, it is not possible to remove or filter more than about 30% of the incoming blood flow rate without causing the blood to become hemoconcentrated and overly viscous. In the embodiment of the present invention described above, by adding the substitution fluid to the blood prior to entering the blood compartment of the second dialyzer, additional fluid (plasma water) is filtered across the second dialyzer membrane, thus enhancing the overall plasma water filtered from the blood side to the dialysate side of both cartridges. The higher substitution rate has the distinct advantage of removing larger molecular weight toxins by convection. In prior art systems operating in a pre-dilution diafiltration mode, the removal of small molecular weight toxins is reduced significantly. This is because the concentration gradient between the blood and the dialysate is reduced whenever fluid is added to the blood prior to flowing through the dialyzer cartridge. Since a scheme similar to a pre-dilution scheme only occurs relative to the second dialyzer in the embodiment described above, the pre-dilution effect is minimized because most of the small molecular weight toxins were removed in the first dialyzer stage which is operated in a post dilution mode. The net effect is an improvement in clearance of small molecular weight toxins compared to pre-dilution diafiltration and an improvement in clearance of large molecular weight toxins when compared to post dilution diafiltration methods using either a single dialyzer or two dialyzers with back filtration occurring in the second dialyzer. A fundamental difference between the two stage hemodiafiltration method described herein and current methods using two dialyzers is that forward filtration of plasma water occurs in both dialyzer stages simultaneously with counter-current flow of dialysate through both dialyzer stages, as opposed to prior art systems which perform forward filtration of plasma water in one dialyzer and reverse-filtration of dialysate in a second dialyzer, with a counter-current flow of dialysate through both dialyzer stages. Additionally, in the present invention, substitution fluid is added directly to the blood stream between the two dialyzer stages, in contrast to the reverse filtering of the substitution fluid through one of the dialyzer membranes in accordance with the prior art.

It has been discovered by the present inventors that the embodiment described above may be further improved by incorporating a control scheme to regulate the amount of filtration in each of the two dialyzer stages. Such control helps avoid the inherent pressure drop which results from operating in a counter-current flow configuration. It has been observed that, without filtration control, the transmembrane pressure (TMP) in the first dialyzer in inherently higher than the TMP in the second dialyzer. Since each dialyzer has a maximum allowable TMP, theoretically, it is possible that the system would operate at a substitute fluid rate exceeding the TMP limit. Further, since the TMP of the second dialyzers is inherently lower than that of the first dialyzer, in essence, the filtering capacity of the second dialyzer may be underutilized. Therefore, by incorporating additional fluid path components, the present invention enables higher, preferably maximal, utilization of the filtering capacity of both dialyzers. The control schemes described in conjunction with the following embodiments are intended to regulate the relative filtration rates of the first and second dialyzers, denoted "UF1" and "UF2", respectively.

Figure 2:
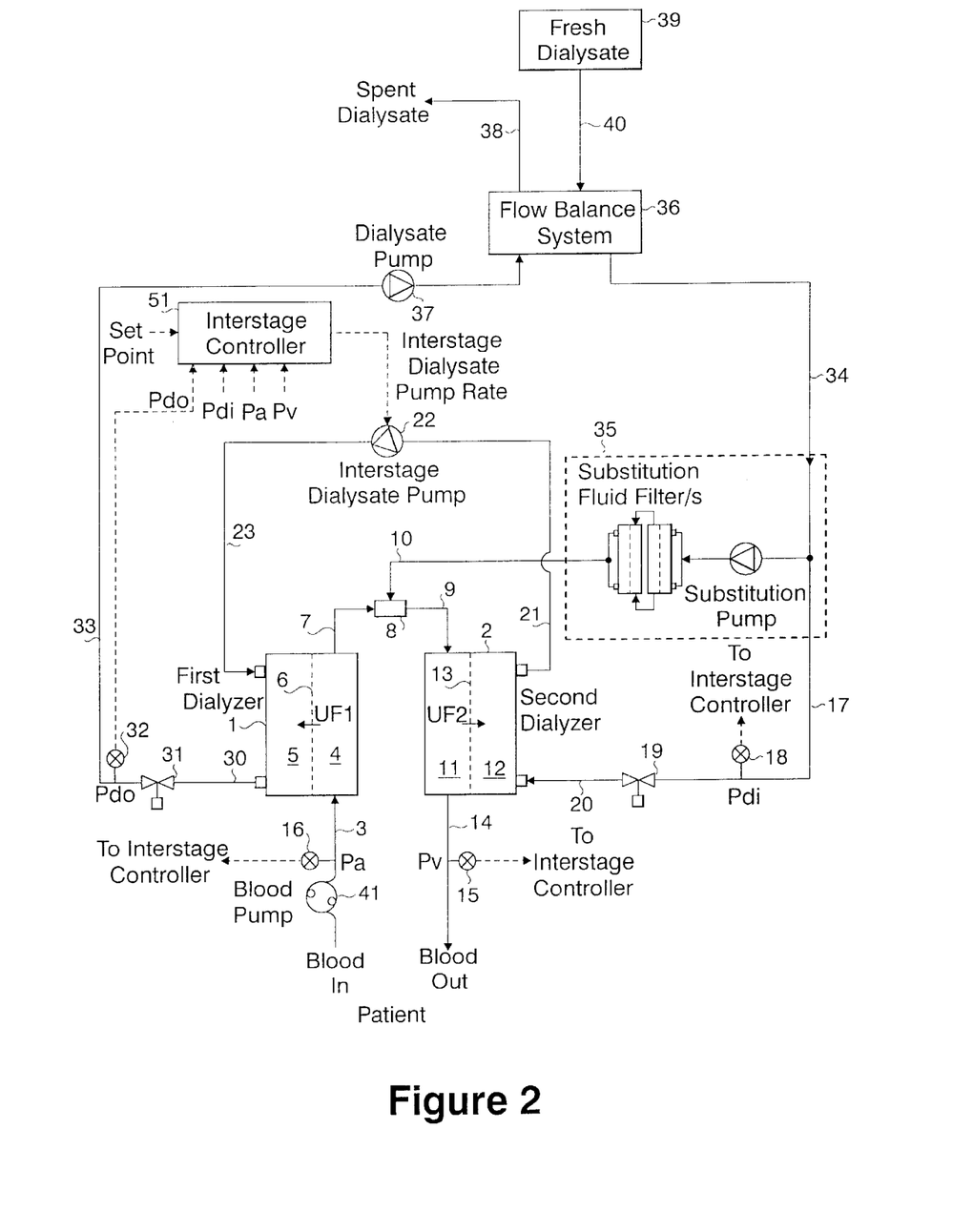
FIG. 2 is a schematic illustration of a two stage hemodiafiltration system in accordance with an embodiment of the invention, using an inter-stage dialysate pump controlled by a feedback loop including pressures inputs.

Reference is now made to FIG. 2 which schematically illustrates a system generally similar to that of FIG. 1 (wherein identical elements are indicated by identical numerals), with the exception that the system of FIG. 2 includes an inter-stage pump, e.g., an inter-stage dialysate pump 22, controlled by closed-loop feedback control using pressure sensor readings, e.g., the inputs indicated in FIG. 2 as Pa, Pv, Pdi, and Pdo, which are received as control inputs by an inter-stage controller 51. The control algorithm used by controller 51 may set the rate of inter-stage pump 22 so that the TMP of the first and second dialyzers are equalized. An example of such a control scheme may be a scheme which defines a control set point "Delta TMP" as the TMP of first dialyzer minus TMP of second dialyzer. A scheme that sets the control set point Delta TMP to some constant value other than zero may also be used. By defining the TMP of each dialyzer stage as a three point pressure measurement, namely blood in (Pa), blood out (Pv), and dialysate in (Pdi) or out (Pdo), the resulting Delta TMP equation may be simplified to the following:

$$\text{Delta } TMP = 0.5*(Pa-Pv)+(Pdi-Pdo)$$

Alternatively, the control algorithm may estimate the total bloodside pressure drop, i.e., (Pa−Pv) in the above equation, based on the blood pump flow rate and substitution pump flow rate. The advantage of this method is that it reduces the number of feedback control inputs being used to two, namely, Pdi and Pdo. For example, the equation for set point Delta TMP may be as follows:

$$\text{Delta } TMP = 0.5*(C1*Qb+C2*Qs+C3*[Qs^2]/Qb)+(Pdi-Pdo)$$

wherein Qb is the blood pump rate, Qs is the substitution fluid rate, and C1, C2 and C3 are constants for a given dialyzer combination that may predict blood side pressure drop (Pa−Pv).

Although FIG. 2 shows an inter-stage dialysate pump, it should be appreciated that a similar control scheme based on pressures can be used to control an inter-stage blood pump that pumps fluid 9 prior to entering second dialyzer 2.

Figure 3A:
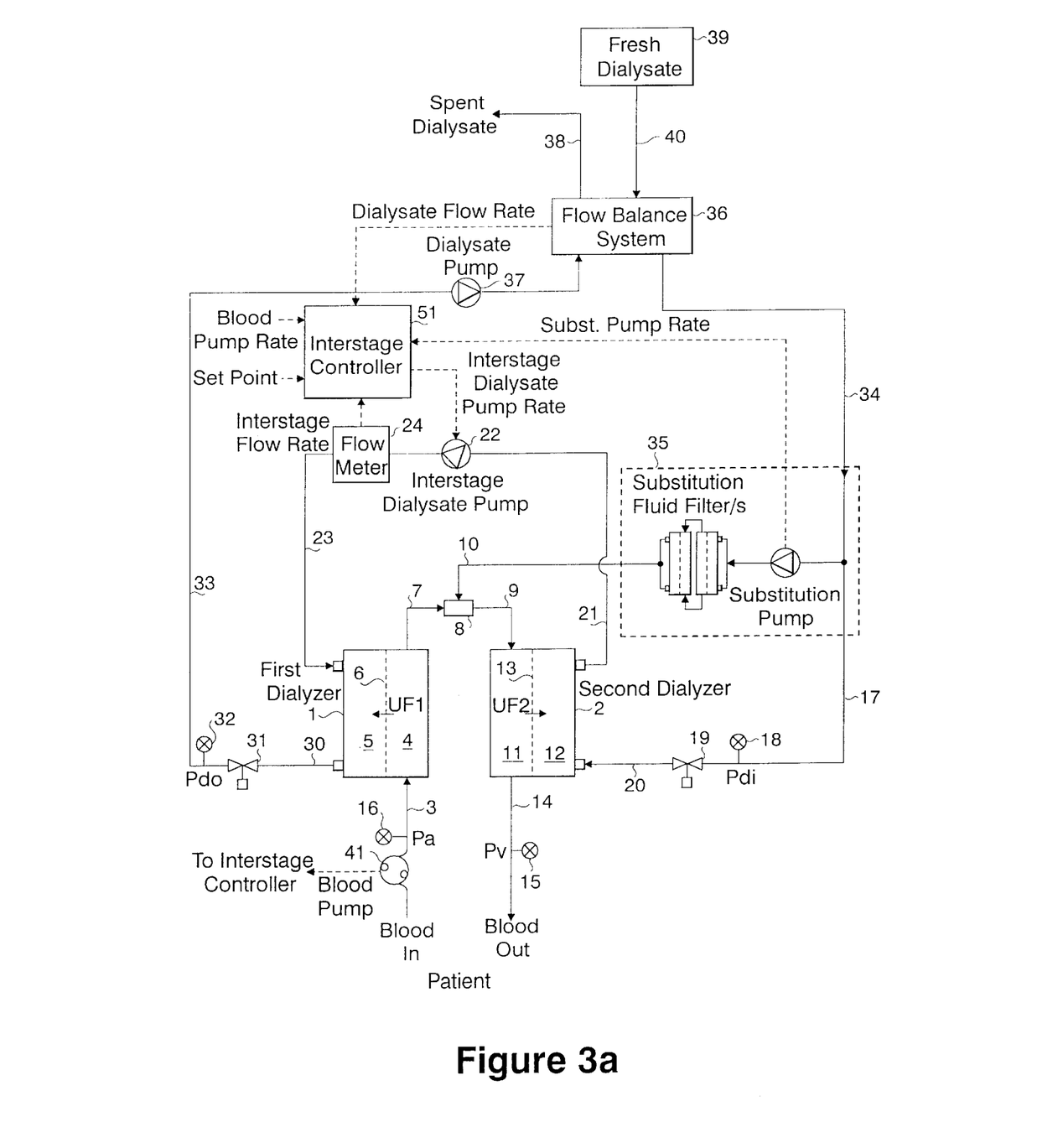
FIG. 3a is a schematic illustration of a two stage hemodiafiltration system in accordance with an embodiment of the invention, using an inter-stage dialysate pump controlled by a feedback loop including an inter-stage flow meter input.

Another embodiment of the invention is schematically illustrated in FIG. 3a, wherein inter-stage pump 22 is controlled by a closed-loop feedback control system using inter-stage flow rate as a feedback control input to an inter-stage controller 51. The scheme illustrated in FIG. 3a shows inter-stage dialysate pump 22 and a dialysate flow meter 24 located in the dialysate path between the two dialyzers. Dialysate flow meter 24 may be of any type suitable for liquid flow, such as turbine flow meters, fixed volume metering chambers, mass flow meters. For control purposes, the dialysate flow rate, substitution pump rate, and blood pump rate may be used as feed-forward control inputs to inter-stage controller 51 to determine the desired set point for the inter-stage flow rate. The calculation for determining the set point for the inter-stage dialysate flow rate (Qd_interstage) may be performed according to the following formula:

$$Qd\_\text{interstage} = Qd - Qs * [R/(1+R)]$$

wherein Qd is the dialysate flow rate, Qs is the substitution fluid flow rate, and R is a constant defined as the desired ratio of UF1/UF2 (i.e. filtration rate in first dialyzer divided by filtration rate of second dialyzer).

Figure 3B:
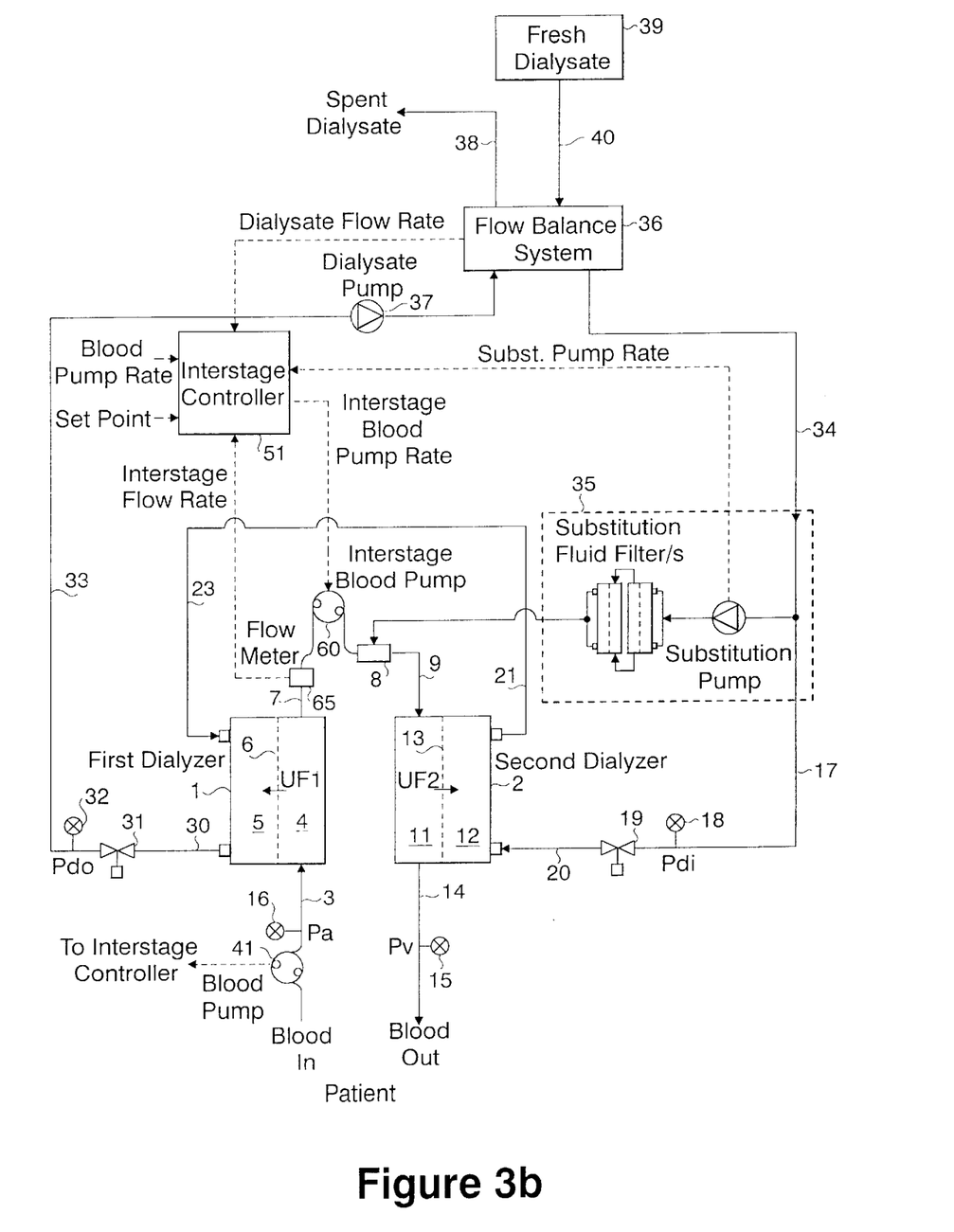
FIG. 3b is a schematic illustration of a two stage hemodiafiltration system in accordance with an embodiment of the invention, using an inter-stage blood pump controlled by a feedback loop including an inter-stage flow meter input.

FIG. 3b schematically illustrates another embodiment of the invention using a control scheme based on monitoring flow rate, with the exception that an inter-stage blood pump 60 is used instead of inter-stage dialysate pump 22. Inter-stage blood pump 60 may be an occluding type, e.g., a peristaltic type pump, or any other suitable pump type known in the art. As shown in FIG. 3b, blood pump 60 may be placed in the blood circuit between first dialyzer 1 and second dialyzer 2. Blood pump 60 may be placed after the blood exits the first dialyzer 1, as shown in FIG. 3b, or after the blood mixes with the substitution fluid 9 prior to entering the second dialyzer 2. Additionally or alternatively, an inter-stage blood flow measuring device 65, for example, an ultrasonic flow meter available from Transonic Systems, Ithica, N.Y., USA, may be placed in the blood circuit between the first and second dialyzers, instead of the inter-stage dialysate flow measuring device 24 described above. The output of blood flow measuring device 65 may be provided as a control input to inter-stage controller 51 which controls the operation of inter-stage blood pump 60. It should be appreciated that, in some embodiments of the invention, a blood flow measuring device similar to device 65 may be used to monitor the blood flow in the embodiment of FIG. 3a, wherein the control input from the device is used by controller 51 to control the operation of dialysate pump 22. Similarly, in some embodiments of the invention, a dialysate flow measuring device similar to device 24 (FIG. 3a) may be used to monitor the dialysate flow in the embodiment of FIG. 3b, wherein the control input from the device is used by controller 51 to control the operation of blood pump 60.

Figure 4:
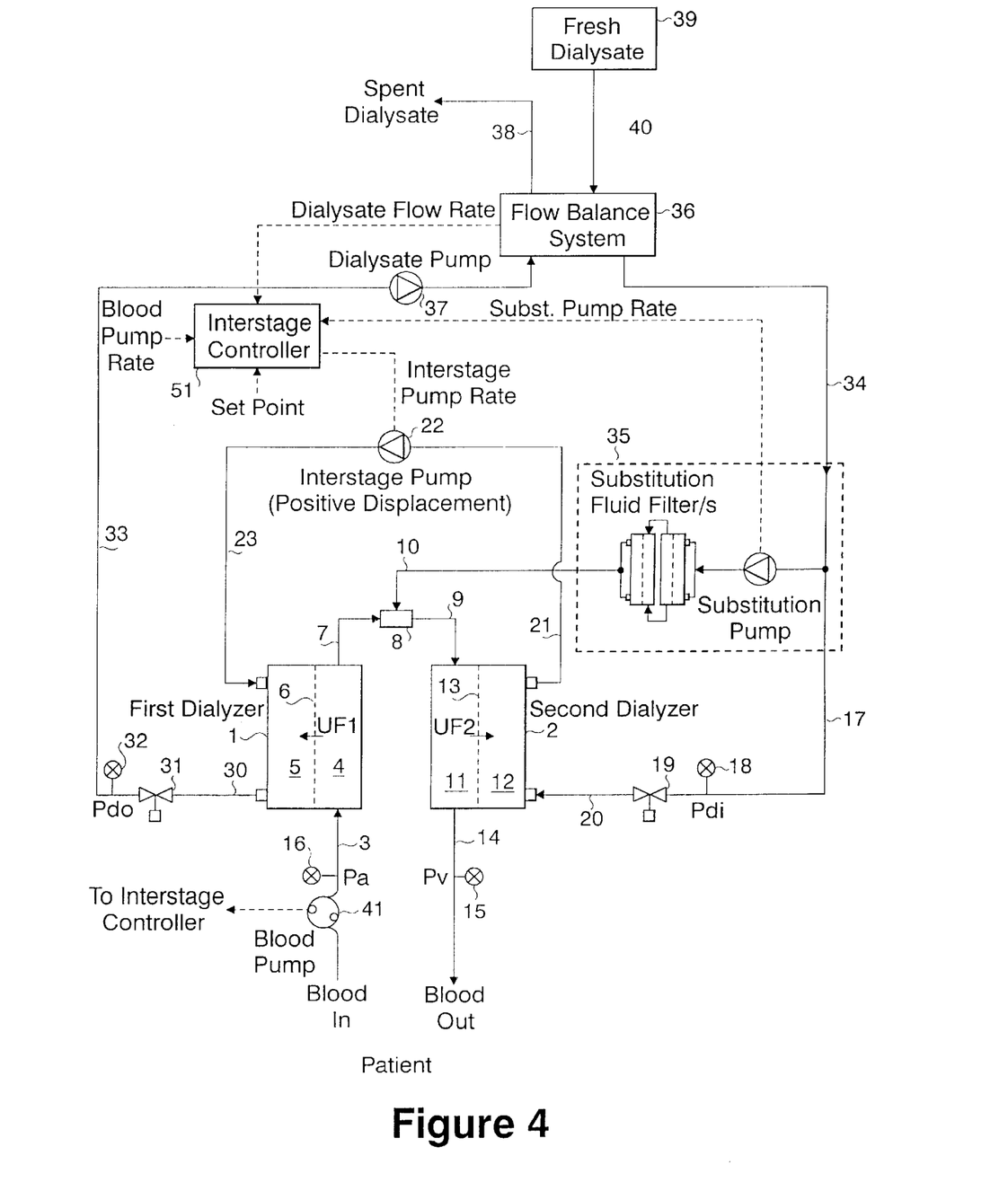
FIG. 4 is a schematic illustration of a two stage hemodiafiltration system in accordance with an embodiment of the invention, using a positive displacement type inter-stage dialysate pump controlled by a feed-forward loop including dialysate, blood, and substitution flow rate control inputs.

Yet another embodiment of the invention is schematically illustrated in FIG. 4. In this embodiment, an inter-stage dialysate pump 22 is a positive displacement type pump controlled by a closed-loop feed-forward scheme. An advantage of this scheme is that it obviates the need to use a flow meter device as part of the control scheme. In the embodiment of FIG. 4, the inputs to inter-stage controller 51 may include dialysate flow rate, substitution pump rate, and blood pump rate. For control purposes, the dialysate flow rate, substitution pump rate, and blood pump rate may be used as feed-forward control inputs to inter-stage controller 51 for determining the desired set point for the inter-stage dialysate flow rate. The point for the inter-stage dialysate flow rate in ("Qd interstage") may be calculated according to the following formula:

$$Qd\ \text{interstage} = Qd - Qs*[R/(1+R)]$$

wherein Qd is the dialysate flow rate, Qs is the substitution flow rate, and R is the desired ratio of UF1/UF2 (i.e., filtration rate of first dialyzer divided by filtration rate of second dialyzer when no net UF is removed from the patient).

Figure 5:
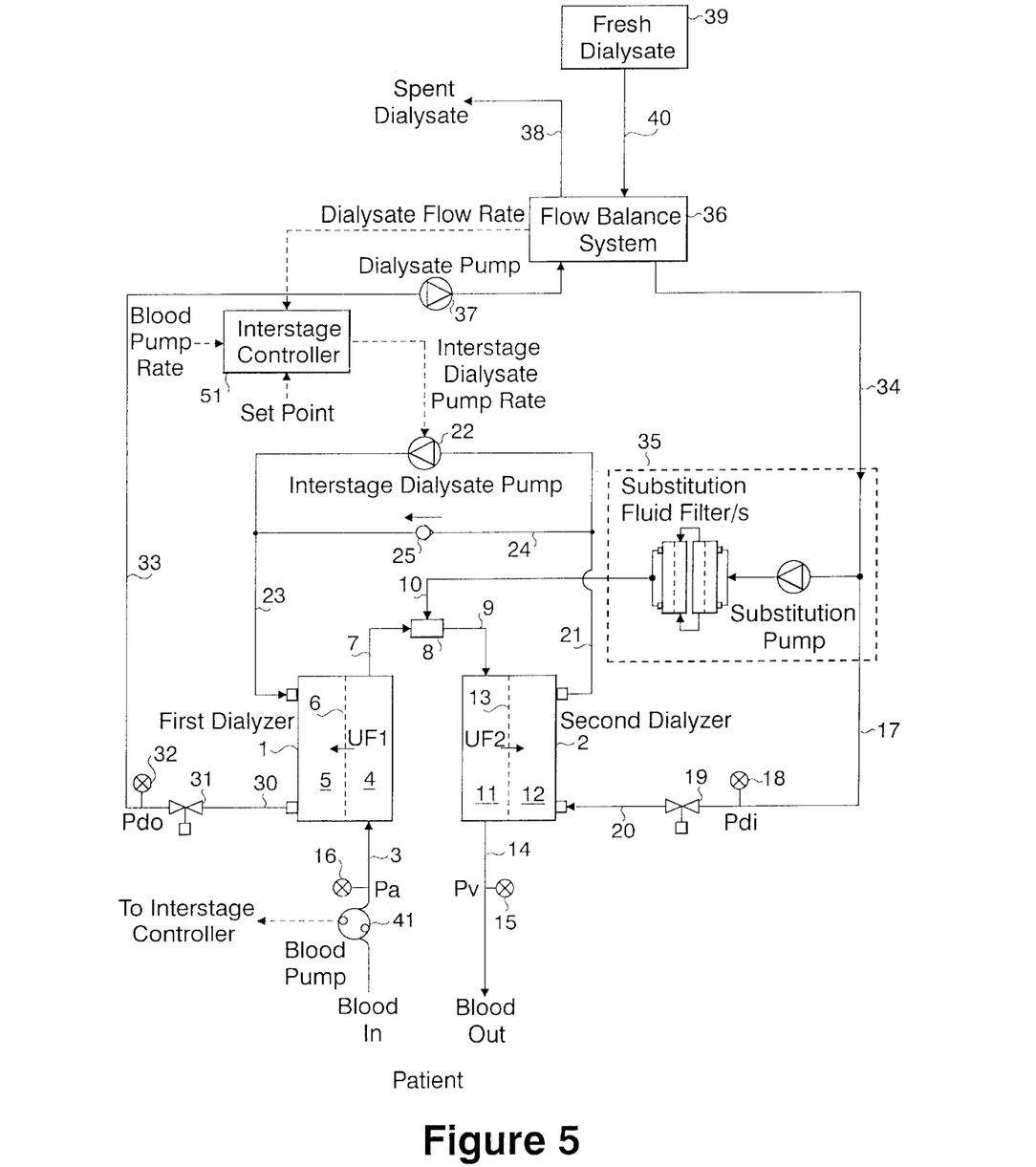
FIG. 5 is a schematic illustration of a two stage hemodiafiltration system in accordance with an embodiment of the invention, using check valve in parallel with an inter-stage dialysate pump, eliminating the need for a substitution flow rate control input.

FIG. 5 schematically illustrates yet another embodiment of the invention, wherein inter-stage dialysate pump 22 is controlled in a closed-loop feed-forward system similar to that described above with the addition of a check valve 25, or a pressure relief valve, which is placed in parallel with inter-stage dialysate pump 22. In addition to the advantages of feed-forward control described above, the configuration of FIG. 5 also has the following advantages. First, the scheme of FIG. 5 does not require use of a positive displacement type pump, which are typically more expensive than non-occluding type pumps. Second, the inter-stage controller in this scheme is independent of substitution rate. Third, the control algorithm for this embodiment may establish the maximum filtration rate for the first dialyzer stage UF1. For example, in this configuration, the inputs to inter-stage controller 51 may include dialysate flow rate and blood pumping rate. For control purposes, the dialysate flow rate and blood pumping rate may be used as feed-forward control inputs to the inter-stage controller for determining a desired set point for the inter-stage dialysate flow rate. For example, in this embodiment, the set point for the inter-stage dialysate flow rate ("Qd interstage") may be calculated based on the following formula:

$$Qd\ \text{interstage} = Qd - M1*Qb$$

wherein Qd is the dialysate flow rate, Qb is the blood pump rate, and M1 is a constant based on the maximum percent of the blood flow rate that is filtered in the first dialyzer stage (UF1).

The operation of the system in accordance with the embodiment of FIG. 5 may be as follows. For a given blood flow rate Qb, dialysate flow rate Qd, and a maximum percentage, M1, of the incoming blood flow to be filtered in the first dialyzer, a desired set point may be determined based on the equation above for the inter-stage dialysate pump rate. The inter-stage dialysate pump may be operated at a specified rate, preferably lower than the dialysate flow rate Qd. For example, at a blood flow rate Qb of 400 ml/min, a dialysate flow Qd of 800 ml/min, and a maximum percentage ultrafiltration (UF) rate M1 of 25% at the first dialyzer, the inter-stage dialysate pump rate may be set to 700 ml/min, based on the calculation: 800−0.25*400ml/min. At zero or low substitution flow rates, the pressure in the dialysate compartment 12 of the second dialyzer will be higher than the pressure of the dialysate compartment 5 of the first dialyzer, despite the pumping action of inter-stage dialysate pump 22. As a result of this pressure difference, a portion of the dialysate fluid flows into conduit 24 and through check valve 25, thus bypassing the inter-stage pump. The rate of filtration in the first dialyzer (UF1) is substantially equal to the dialysate flow rate (Qd) minus the sum of the inter-stage dialysate pump rate (Qd_interstage) and the flow rate through the check valve (Qcv). As the substitution flow rate (Qs) is increased, the pressure in the dialysate compartment 12 of the second dialyzer is decreased. At some point, this pressure becomes lower than the pressure in dialysate compartment 5 of first dialyzer 1. At this point, the flow rate through the check valve (Qcv) is reduced to substantially zero and, thus, the resulting filtration rate of the first dialyzer (UF1) is substantially equal to the dialysate flow rate (Qd) minus the inter-stage dialysate pump rate (Qd interstage). An increase in the substitution fluid flow rate decreases the pressure in the dialysate compartment of the second dialyzer 2 causing an increased filtration (UF2). Since the inter-stage dialysate pump rate has not changed, the pressure in dialysate compartment 5 of the first dialyzer remains relatively constant and, thus, does not affect the filtration rate in the first dialyzer (UF1). According to this scheme, the amount of filtration in the first dialyzer stage is limited to a maximum value, "UF1 max", that may be calculated using the following formula:

$$UF1\ \text{max} = M1*Qb$$

Figure 6:
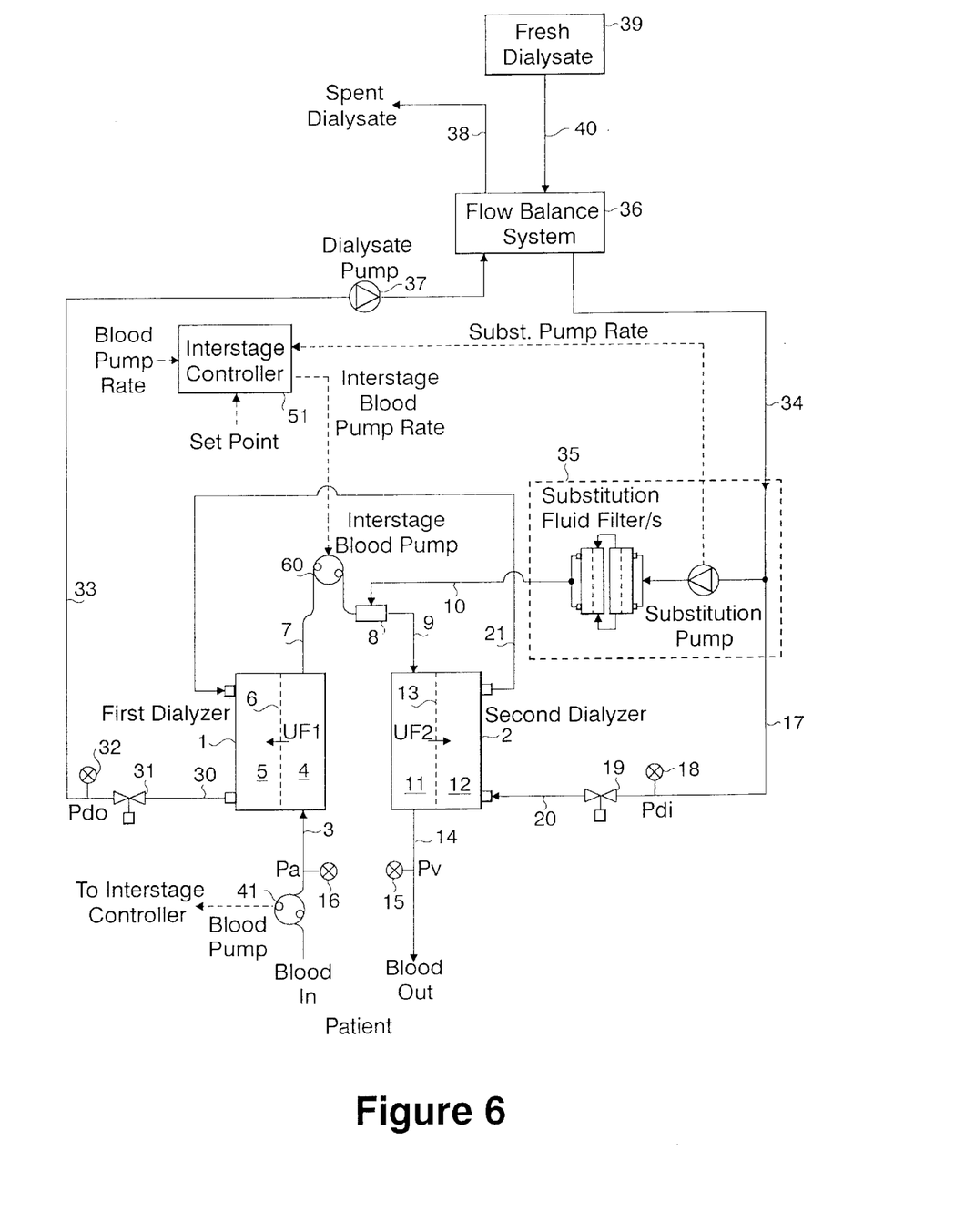
FIG. 6 is a schematic illustration of a two stage hemodiafiltration system in accordance with an embodiment of the invention, using a positive displacement type inter-stage blood pump controlled by a feed-forward loop including dialysate, blood, and substitution flow rate control inputs.
Figure 7:
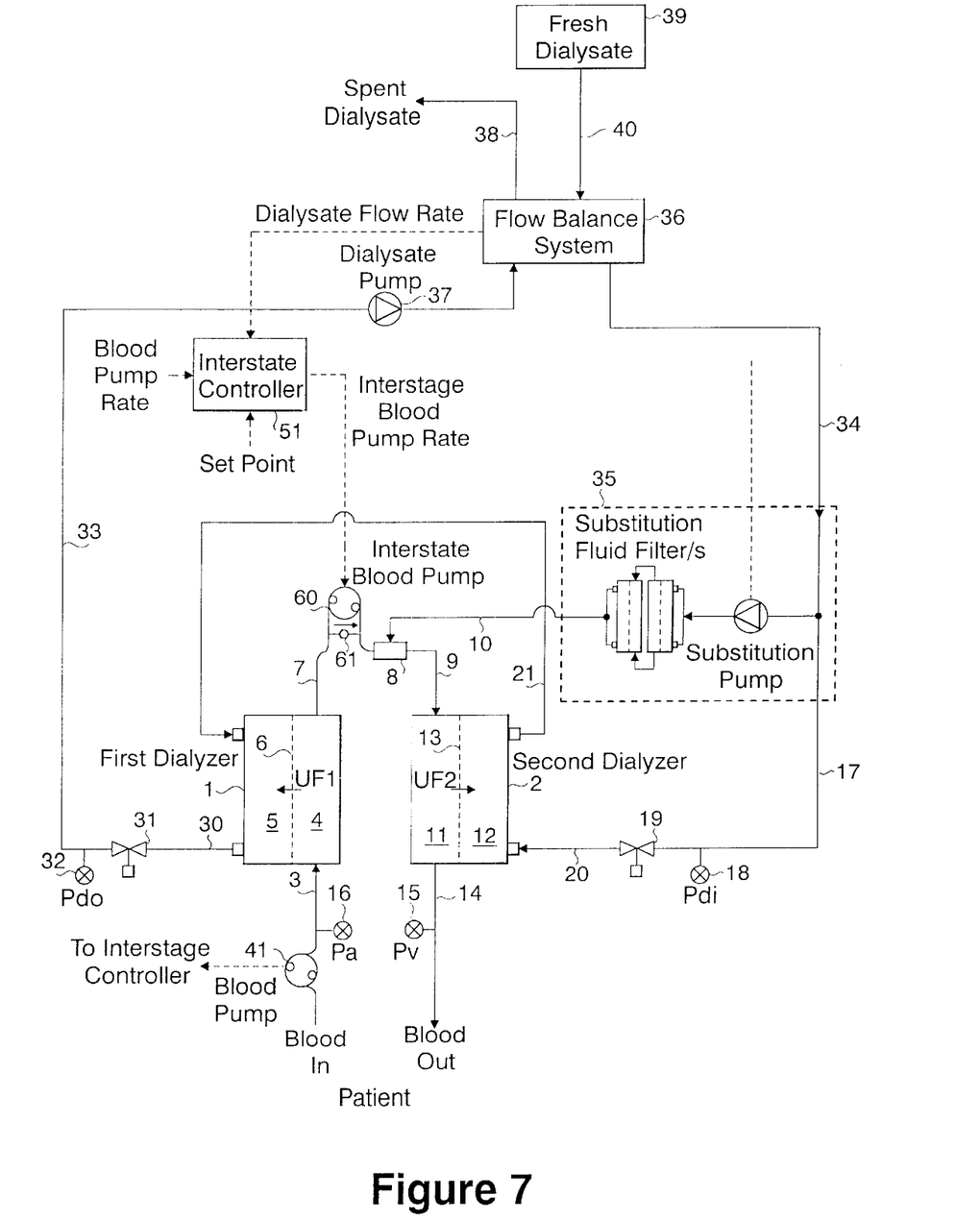
FIG. 7 is a schematic illustration of a two stage hemodiafiltration system in accordance with an embodiment of the invention, using a check valve in parallel with an inter-stage blood pump, eliminating the need for substitution flow rate control input.

FIGS. 6 and 7 describe two additional embodiments of the invention, using control schemes generally similar to those used in the embodiments of FIGS. 4 and 5, respectively; with the exception that inter-stage blood pump 60, which may be identical to the blood-pump described above with reference to the embodiment of FIG. 3b, is used instead of an inter-stage dialysate pump. Inter-stage blood pump 60 may be an occluding type, e.g., a peristaltic type pump, or any suitable pump known in the art. In the embodiment of FIG. 6, inter-stage blood pump 60 is located on the blood tubing segment 7 after the blood exits the first dialyzer. In this configuration, the inputs to inter-stage controller 51 may include the substitution fluid pumping rate and the blood pumping rate. For control purposes, substitution pumping rate and blood pumping rate may be used as feed-forward control inputs to inter-stage controller 51 for determining the desired set point for the inter-stage blood flow rate. The set point for the inter-stage blood flow rate ("Qb inter-stage") may be calculated using the following formula:

$$Qb\_\text{interstage} = Qb - Qs*[R/(1+R)]$$

wherein Qb is the inlet blood flow rate, Qs is the substitution flow rate, and R is constant defined as the desired ratio of UF1/UF2 (i.e. filtration rate in first dialyzer divided by filtration rate of second dialyzer when no net UF is removed from the patient).

In the embodiment of FIG. 7, check valve 61 (which is preferably of a type suitable for blood contact) is placed in parallel with inter-stage blood pump 60. This has the advantage of allowing blood flow to be shunted past the inter-stage blood pump, thus avoiding pressure build ups that may occur when the two blood pumps, 41 and 60, are running at different rates and the dialysate flow is operated at an "isolated" (or "bypass") mode. Both pumps 41 and 60 are preferably occluding type pumps. In this control scheme, the input to inter-stage controller 51 may include the blood pumping rate Qb. For control purposes, the blood pumping rate may be used as a feed-forward input to the inter-stage controller to determine the desired set point for the inter-stage blood flow rate. The set point for the inter-stage blood flow rate ("Qb interstage") may be calculated, for example, using the following formula:

$$Qb\ \text{interstage} = Qb - M1*Qb$$

wherein Qb is the blood pump rate, and M1 is a constant defined as the maximum percent of the blood flow rate that is filtered in the first dialyzer stage (UF1).

The operation of the embodiment of FIG. 7 is described as follows. For a given blood pump rate Qb and maximum percent of the incoming blood flow that is to be filtered in the first dialyzer M1, a set point for the set point for the inter-stage blood pump rate is determined based on the above equation. The inter-stage blood pump may be operated at a specified rate, preferably lower than the inlet blood flow rate Qb. For example, at a blood flow rate of 400 ml/min and maximum UF percentage M1 of 25% at the first dialyzer, the inter-stage blood pump rate may be set about 300 ml/min, based on the calculation: 400−0.25*400 ml/min. At zero or low substitution flow rates, the pressure in the blood compartment 4 of the first dialyzer 1 is higher than the pressure of the blood compartment 11 of second dialyzer 2, despite the pumping action of the inter-stage blood pump 60. As a result of this pressure difference, a portion of the blood flows through check valve 61, thus bypassing inter-stage blood pump 60. At this point, the filtration rate in the first dialyzer (UF1) is substantially equal to the blood flow rate (Qb) minus the sum of the inter-stage blood pump rate (Qb_interstage) and the flow rate through the check valve (Qcv). As the substitution flow rate (Qs) is increased, there is an increase in pressure downstream of the inter-stage blood pump due to the influx of substitution fluid into mixing chamber 8. At some point, this pressure becomes higher than the inlet pressure of the inter-stage blood pump. This reduces the flow rate through check valve (Qcv) to substantially zero, and the resulting filtration rate in the first dialyzer (UF1) is substantially equal to the inlet blood flow rate (Qb) minus the inter-stage blood pump rate (Qb_interstage). A subsequent increase in substitution rate causes a pressure increase downstream of the inter-stage blood pump and in the blood compartment of the second dialyzer 2 causing an increased filtration rate (UF2). Since the inter-stage blood pump rate has not changed, the pressure in blood compartment 4 of first dialyzer 1 remains relatively constant and, thus, does not affect the filtration rate in the first dialyzer (UF1). Consequently, the filtration rate in the first dialyzer stage is limited to a maximum value ("UF1 max") that may be calculated using the following formula:

$$UF1\ max = M1*Qb$$

Figure 8:
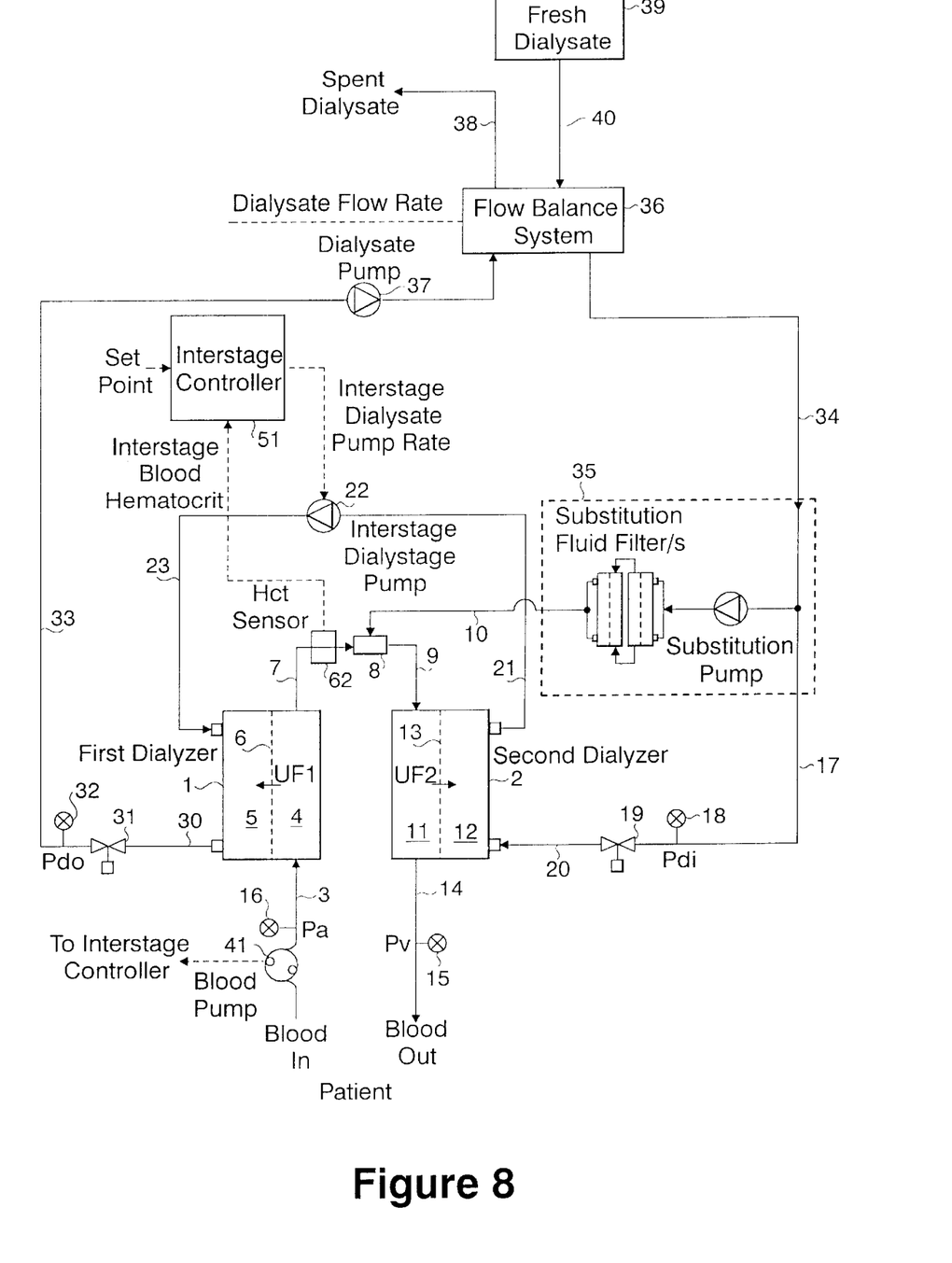
FIG. 8 is a schematic illustration of a two stage hemodiafiltration system in accordance with an embodiment of the invention, using an inter-stage pump controlled by a feedback loop including an inter-stage blood hematocrit measurement control input.

FIG. 8 schematically illustrates yet another embodiment of the invention, wherein inter-stage dialysate pump 22 is controlled by a closed-loop feedback control system using a blood hematocrit sensor as a feedback control input to inter-stage controller 51. The system illustrated in FIG. 8 includes an in-line blood hematocrit sensor 62 located in the blood path 7 after the blood exits first dialyzer 1. Blood hematocrit sensor 62 may be of a non-invasive type, for example, the "Crit-Line" sensor available from Inline Diagnostics, Kaysville, Utah, USA. Control of the inter-stage dialysate pump is based on a set point for the inter-stage blood hematocrit. The advantage of this scheme is that the system can achieve a higher effective filtration rate in the first dialyzer for situations in which the hematocrit level of the entering blood is below normal, thus maximizing removal efficiency. Additionally, for those situations where the entering blood hematocrit level is above normal, the system does not over-hemoconcentrate the blood in the first dialyzer.

It should be appreciated that although the embodiment of FIG. 8 is described in conjunction with an inter-stage dialysate pump, a similar control scheme based inter-stage blood hematocrit exiting the first dialyzer may be readily implemented to control an inter-stage blood pump instead of the inter-stage dialysate pump. For example, the inter-stage blood pump may be placed after the blood exits the first dialyzer 1 or after the blood is mixed with the substitution fluid 9 prior to entering the second dialyzer 2.

It will be appreciated by persons skilled in the art to which this invention pertains that the invention is not limited to the preferred embodiments and configurations described above and with reference to the accompanying drawings. Rather, the scope of the invention is limited only by the following claims.

What is claimed is:

1. In a blood dialysis system including a source of substitution fluid and a blood dialysis machine, a hemodiafiltration system comprising:
   a first dialyzer comprising:
      a first semi-permeable membrane partitioning said first dialyzer into:
         a first blood compartment having a first blood inlet which receives blood to be cleaned and a first blood outlet which expels partially diafiltered blood; and
         a first dialysate compartment having a first dialysate inlet and a first dialysate outlet;
   means for mixing said partially diafiltered blood with substitution fluid from said source to obtain a blood/substitution fluid mixture;
   a second dialyzer comprising:
      a second semi-permeable membrane partitioning said second dialyzer into:
         a second blood compartment having a second blood inlet which receives said blood/substitution fluid mixture and a second blood outlet which expels diafiltered blood; and
         a second dialysate compartment having a second dialysate inlet and a second dialysate outlet; and
   means for regulating filtration rates of said first and second dialyzers.

2. A hemodiafiltration system according to claim 1, wherein said means for regulating the filtration rates includes an inter-stage dialysate pump which pumps dialysate between said second dialysate compartment and said first dialysate compartment, thereby to regulate the filtration rates.

3. A hemodiafiltration system according to claim 1, wherein said means for regulating the filtration rates includes an inter-stage blood pump which pumps fluid between said first blood compartment and said second blood compartment, thereby to regulate the filtration rates.

4. A hemodiafiltration system according to claim 2, wherein said means for regulating the filtration rates includes a control unit which controls the operation of said inter-stage dialysate pump based on an input responsive to the dialysate flow rate between said second dialysate compartment and said first dialysate compartment.

5. A hemodiafiltration system according to claim 3, wherein said means for regulating the filtration rates includes a control unit which controls the operation of said inter-stage blood pump based on an input responsive to the fluid flow rate between said first blood compartment and said second blood compartment.

6. A hemodiafiltration system according to claim 2, wherein said means for regulating the filtration rates includes a control unit which controls the operation of said inter-stage dialysate pump based on an input responsive to a transmembrane pressure of at least one of said first and second dialyzers.

7. A hemodiafiltration system according to claim 3, wherein said means for regulating the filtration rates includes a control unit which controls the operation of said inter-stage blood pump based on an input responsive to a transmembrane pressure of at least one of said first and second dialyzers.

8. A hemodiafiltration system according to claim 2, wherein said means for regulating the filtration rates includes a control unit which controls the operation of said inter-stage dialysate pump based on an input responsive to the hematocrit level of the blood being cleaned.

9. A hemodiafiltration system according to claim 3, wherein the means for regulating the relative filtration rates includes a control unit which controls the operation of said inter-stage blood pump based on an input responsive to the hematocrit level of the blood being cleaned.

10. A method of hemodiafiltration comprising the steps of:
    receiving a blood inflow;
    diafiltering said blood inflow to provide a partially diafiltered blood outflow;
    mixing said partially diafiltered blood outflow with a substitution fluid to provide a blood/substitution fluid mixture; and
    diafiltering said blood/substitution fluid mixture.

11. A method according to claim 10 further comprising the step of pumping said blood/substitution fluid mixture before diafiltering said mixture.

12. A method according to claim 10 further comprising, before the step of mixing said diafiltered blood outflow, the step of pumping said partially diafiltered blood outflow.

13. A method according to claim 11 further comprising the step of controlling the rate of said pumping based on an input responsive to a flow rate of the blood being cleaned.

14. A method according to claim 12 further comprising the step of controlling the rate of said pumping based on an input responsive to a flow rate of the blood being cleaned.

15. A method according to claim 11 further comprising the step of controlling the rate of said pumping based on an input responsive to a transmembrane pressure effective during at least one of said diafiltering of the blood inflow and said diafiltering of the blood/substitution fluid mixture.

16. A method according to claim 12 further comprising the step of controlling the rate of said pumping based on an input responsive to a transmembrane pressure effective during at least one of said diafiltering of the blood inflow and said diafiltering of the blood/substitution fluid mixture.

17. A method according to claim 11 further comprising the step of controlling the rate of said pumping based on an input responsive to the hematocrit level of the blood being cleaned.

18. A method according to claim 12 further comprising the step of controlling the rate of said pumping based on an input responsive to the hematocrit level of the blood being cleaned.

19. A method according to claim 10 wherein the step of diafiltering said blood/substitution fluid mixture comprises the step providing a first countercurrent flow of a dialysate solution in diffusion communication with said blood/substitution fluid mixture, and wherein the step of diafiltering said blood inflow comprises the step of providing a second countercurrent flow of the dialysate solution in diffusion communication with said blood inflow.

20. A method according to claim 19 further comprising the step of pumping said dialysate solution after providing said first countercurrent and before providing said second countercurrent.

21. A method according to claim 20 further comprising the step of controlling the rate of said pumping based on an input responsive to a flow rate of the blood being cleaned.

22. A method according to claim 20 further comprising the step of controlling the rate of said pumping based on an input responsive to a transmembrane pressure effective during at least one of said diafiltering of the blood inflow and said diafiltering of the blood/substitution fluid mixture.

23. A method according to claim 20 further comprising the step of controlling the rate of said pumping based on an input responsive to the hematocrit level of the blood being cleaned.

24. A method according to claim 19 further comprising, before the step of providing a first countercurrent flow, the step of sterilizing said dialysate solution, thereby to generate said substitution fluid.

25. A method according to claim 20 further comprising, before the step of providing a first countercurrent flow, the step of sterilizing said dialysate solution, thereby to generate said substitution fluid.

26. A hemodiafiltration device comprising:
    a first dialyzer including:
        a first semi-permeable membrane defining a first blood compartment and a first dialysate compartment;
        said first blood compartment having a first blood inlet which receives blood and a first blood outlet which discharges blood having a first concentration of toxins; and
        said first dialysate compartment having a first dialysate inlet and a first dialysate outlet;
    means for mixing said blood discharged from said first blood compartment with substitution fluid from a source of substitution fluid to obtain a blood/substitution fluid mixture;
    a second dialyzer including:
        a second semi-permeable membrane defining a second blood compartment and a second dialysate compartment;
        said second blood compartment having a second blood inlet which receives said blood/substitution fluid mixture and a second blood outlet which discharges blood having a second concentration of toxins, the first concentration of toxins being greater than the second concentration of toxins; and
        said second dialysate compartment having a second dialysate inlet and a second dialysate outlet; and
    a control unit for regulating filtration rates across the first and second semi-permeable membranes in the first and second dialyzers, respectively.

27. The hemodiafiltration device according to claim 26, wherein the control unit regulates the filtration rates in response to receiving an input representing a transmembrane pressure of each of the first and second dialyzers.

28. The hemodiafiltration device according to claim 26, wherein the control unit is a feedback control loop that regulates the filtration rates based on received input.

29. The hemodiafiltration device according to claim 26, further including an inter-stage pump for pumping one of (a) dialysate fluid between said first dialysate compartment and said second dialysate compartment and (b) blood between said first blood compartment and said second blood compartment, wherein said control unit controls the operation of the inter-stage pump based on an input received by said control unit.

30. The hemodiafiltration device according to claim 29, wherein the input received is selected from the group consisting of (a) an input responsive to the blood flow rate between said first blood compartment and said second blood compartment; (b) an input responsive to the dialysate flow rate between said first dialysate compartment and said second dialysate compartment; (c) an input responsive to a transmembrane pressure of at least one of said first and second dialyzers; and (d) an input responsive to a hematocrit level of the blood.

31. A method of hemodiafiltration comprising the steps of:

receiving a blood inflow;

diafiltering said blood inflow in a first stage to provide a partially diafiltered blood outflow;

mixing said partially diafiltered blood outflow with a substitution fluid to provide a blood/substitution fluid mixture;

diafiltering said blood/substitution fluid mixture in a second stage; and controlling filtration rates of the diafiltering of said blood inflow and the diafiltering of said blood/substitution fluid mixture by regulating one of a blood flow rate and a dialysate flow rate.

32. The method of claim 31, where the step of controlling the filtration rates includes the step of controlling an inter-stage pump for pumping one of (a) dialysate fluid between said first and second stages and (b) blood between said first and second stages, wherein operation of said inter-stage pump is controlled with a control unit based on an input received by said control unit.

33. The method of claim 32, wherein the input received is selected from the group consisting of (a) an input responsive to the blood flow rate between said first stage and said second stage; (b) an input responsive to the dialysate flow rate between said first stage and said second stage; (c) an input responsive to a transmembrane pressure of at least one of said first and second stages; and (d) an input responsive to a hematocrit level of the blood.

* * * * *